(12) United States Patent
Ponceblanc et al.

(10) Patent No.: US 6,545,179 B2
(45) Date of Patent: Apr. 8, 2003

(54) PROCESS FOR THE PRODUCTION OF METHIONINE

(75) Inventors: Herve Ponceblanc, Villerubanne (FR); Jean-Christophe Rossi, Villeneuve les Maguelone (FR); Phillippe Laval, Paris (FR); Georges Gros, Antony (FR)

(73) Assignee: Aventis Animal Nutrition, SA, Antony (FR)

( * ) Notice: Subject to any disclaimer, the term of this patent is extended or adjusted under 35 U.S.C. 154(b) by 0 days.

(21) Appl. No.: 09/782,416

(22) Filed: Feb. 13, 2001

(65) Prior Publication Data

US 2001/0037038 A1 Nov. 1, 2001

(30) Foreign Application Priority Data

Feb. 15, 2000 (WO) ............................. PCT/EP00/01528
Feb. 15, 2000 (WO) ............................. PCT/EP00/01529

(51) Int. Cl.[7] ............... C07C 321/00; C07C 323/00; C07C 381/00
(52) U.S. Cl. ......................................... 562/559
(58) Field of Search .................................. 562/559

(56) References Cited

U.S. PATENT DOCUMENTS 5,672,745 A * 9/1997 Hassberg et al. ............ 562/559

FOREIGN PATENT DOCUMENTS

| EP | WO 94/08957 | 4/1994 |
| FR | 2 772 026 | 6/1999 |
| JP | 3-93753 | * 9/1989 |

OTHER PUBLICATIONS

English abstract (as abstracted by CAPLUS) of JP 03093753. Mizuno et al (Apr. 1991).*
English language abstract of JP 03093754 (Apr. 18, 1991).
English language abstract of JP 03093753 (Apr. 18, 1991).
English language abstract of FR 2 772 026 from Orbit (Jun 11, 1999).

* cited by examiner

Primary Examiner—Mukund J. Shah
Assistant Examiner—Zachary C. Tucker
(74) Attorney, Agent, or Firm—Connolly Bove Lodge & Hutz LLP

(57) ABSTRACT

A process for the production of methionine which comprises (a) hydrolysing the methionine amide in the presence of a catalyst comprising titanium to produce ammonium methioninate, said catalyst having a porosity of from 5 to 1000 nm, a total pore volume of from 0.2 to 0.55 $cm^3/g$ and a surface area of from 30 to 150 $m^2/g$, and (b) a second step of recuperating methionine from the ammonium methioninate salt by removing ammonia. Also claimed is an industrial process for the production of methionine incorporating the aforementioned hydrolysis.

14 Claims, 6 Drawing Sheets

PROCESS FOR THE PRODUCTION OF METHIONINE

The present invention relates to a process for the production of methionine through the hydrolysis of methionine amide using a catalyst comprising titanium and to use of the process for the industrial production of methionine comprising low amounts of and in some cases, substantially no salt by-products The hydrolysis of the methionine amide to produce the methionine is a known process. In particular, European Patent Application No228938 discloses a process for the production of methionine by the hydrolysis of the methionine amide using a strong base. A problem with this process is that the acidification step uses a strong acid which results in the co-production of mineral salts such as carbonates, chlorides or sulphates. An additional purification step is generally required to remove the salt.

French Patent Application No. 9814000 attempts to overcome the aforementioned problem through the use of a titanium catalyst in the hydrolysis reaction. The use of a titanium based catalyst is also disclosed in Japanese patent applications 03093753, 03093754, 03093755, 03093756.

We have now found that methionine can be produced in high yields using a specific titanium catalyst. Accordingly, the present invention provides a process for the production of methionine which comprises (a) hydrolysing methionine amide in the presence of a catalyst comprising titanium to produce ammonium methioninate, said catalyst having a porosity of from 5 to 1000 nm, a total pore volume of from 0.2 to 0.55 cm$^3$/g and a surface area of from 30 to 150 m$^2$/g, and (b) a second step of recuperating methionine from the ammonium methioninate salt by removing ammonia.

Figure 1:
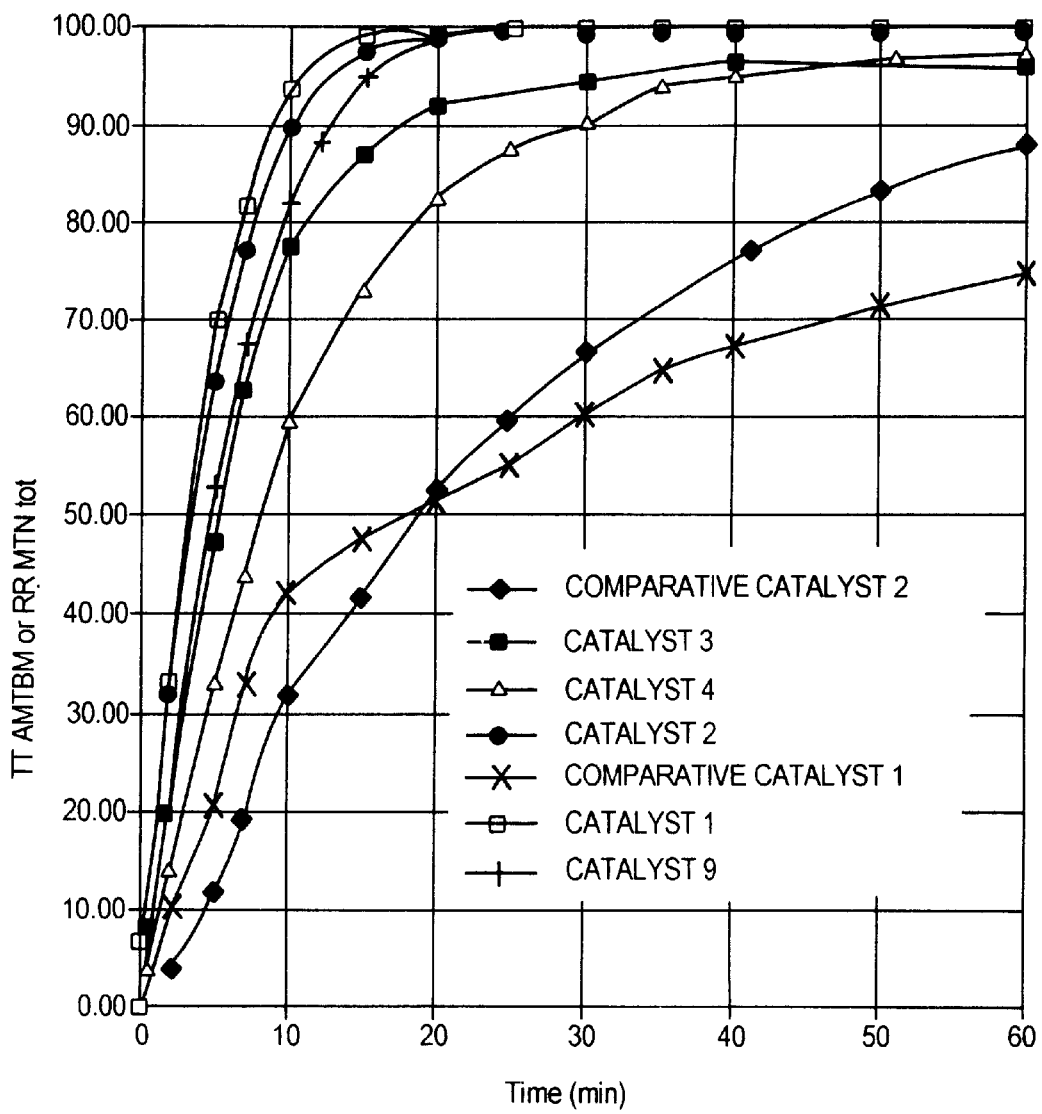
FIG. 1 is a graph of TT AMTBM versus time for the catalysts of Example 2.

The process of the present invention provides the advantage over the known prior art processes for the production of methionine in that the methionine amide can be completely converted to methionine without the need for additional treatment.

The process of the present invention is directed to the hydrolysis of methionine amide. Suitably, the amide is present in an aqueous solution in an amount of from 0.01 to 2 mol/kg, preferably from 0.5 to 1 mol/kg.

The process of the present invention is a catalysed process using a titanium-containing catalyst. The catalyst has a porosity of from 5 to 1000 nm. For the purposes of the present invention, porosity is defined as the distribution of the pores within the crystallites which constitute the agglomerates. Preferably, the catalyst has a macroporous distribution of from 5 to 100 nm and from 20 to 1000 nm. It is preferred that the distribution is bimodal.

The catalyst has a pore volume as determined by mercury porosimetry of from 0.2 to 0.55 cm$^3$/g, preferably from 0.25 to 0.45 cm$^3$/g.

The catalyst must also have a surface area, as determined by B.E.T., of from 30 to 150 m$^2$/g, preferably from 40 to 120 m$^2$/g.

The catalyst may be any used in the powdered form or in the form of particles or granules or the like. Where the catalyst is used in the process in the form of granules or particles any suitable shape may be used, for example extrudates, spherical particles, and tablets. We have also found that the catalyst is effective when used in the form of extrudates having the particular shape of either a three leaf or a four leaf clover. Suitably, the catalyst particles have a diameter of from 0.05 to 4 mm, preferably from 0.5 to 2 mm.

The catalyst may comprise titanium as the sole metal or may comprise one or more additional metals. Where titanium is the only metal, the catalyst may be titanium oxide ($TiO_2$). Where the catalyst comprises additional metals, suitable catalysts include Ti—W, Ti—Mo, Ti—Si—W, Ti—Nb—Mo, Ti—Zr, Ti—Al, Ti—Cr, Ti—Zn and Ti—V.

The catalyst may be prepared by any suitable method, for example mixing the dry ingredients, calcining at a suitable temperature and forming the desired shape. Alternatively, after mixing and/or calcining the dry ingredients, water and/or an acid may be added to the titanium powder to form a paste. After kneading, the paste may be extruded and the resulting product calcined.

The amount of catalyst used in the process will depend on the nature of the process and on the physical nature of the catalyst. Where the catalyst is used in the powdered form a suitable amount may be from 0.1 to 2 grams of catalyst per gram of amide, preferably from 0.5 to 1.5 g. Where the catalyst is used in the particulate or granular form and on a continuous basis, the contact time may be from 0.5 to 60 minutes, preferably from 5 to 30 minutes.

The catalyst may deactivate after a long period of use in the process. Re-generation may be carried out in-situ or ex-situ. Where the regeneration is carried out in-situ, the catalyst may be contacted with water or acidified water i.e. water containing 0.01 to 5% mineral acid, at a temperature from ambient temperature to the operating temperature of the process, for example from ambient temperature up to 130° C. Where the regeneration is carried out ex-situ, this regeneration may be carried out by heating in an oxygen-containing gas such as air or pure oxygen at a temperature of from 200 to 500° C., preferably from 300 to 400° C.

The process of the present invention may suitably be carried out at a temperature of from 50 to 150° C., preferably from 80 to 130° C. and under a pressure of from 1 to 10 bar, preferably from 1 to 5 bar.

In the second step of the reaction, methionine is liberated from the ammonium methioninate salt by removing ammonia. This may be accomplished by any suitable method, for example stripping.

The process may be carried out either as a batch process or as a continuous process. Preferably, the process is carried out as continuous plug flow process and using one or two or more reactors connected in series. This configuration is particularly preferred since it requires less catalyst, an advantage which is particularly favourable in an industrial process. The process may be carried out in any suitable reactor, for example a fixed or fluidised bed reactor. Preferably, the process is carried out in a fixed bed reactor.

The amide may be obtained from the known prior art processes in which there is a first step which comprises reacting 2-hydroxy-4-methylthio-butanenitrile (HMTBN) with ammonia or an ammonium solution to produce 2-amino-4-methylthio butanenitrile (AMTBN). The 2-amino-4-methylthio butanenitrile product may then be reacted with a ketone in the presence of an alkali metal hydroxide to produce methionine amide (AMTBM). The process of the present invention may be incorporated into the known processes to provide a novel industrial process for the production of methionine.

Thus, according to further aspect of the present invention there is provided a process for the production of methionine, said process capable of industrial application, which comprises (a) contacting 2-hydroxy-4-methylthio butanenitrile with ammonia or a solution containing ammonia to produce a first product stream comprising 2-amino-4-methylthio butanenitrile, (b) contacting the said first product stream with a ketone and an alkali metal hydroxide to produce a second product stream comprising methionine amide, unreacted ketone, ammonia and water.

(c) removing the unreacted ketone, ammonia and water from the second product stream (d) hydrolysing the methionine amide in the presence of a catalyst comprising titanium to produce a third product stream comprising ammonium methioninate, said catalyst having a porosity of from 5 to 1000 nm, a total pore volume of from 0.2 to 0.55 cm$^3$/g and a surface area of from 30 to 150 m$^2$/g, and (e) liberating methionine from the ammonium methioninate salt.

This process capable of being operated on an industrial scale involves the conversion of 2-hydroxy-4-methylthio butanenitrile. This starting material may be obtained by any suitable method, for example by the reaction between hydrocyanide (HCN) and methyl 4-methylthio-propanal aldehyde as disclosed in European Patent Application No. 739870, herein incorporated by reference.

In the first step of this industrial process of the present invention, the 2-hydroxy-4-methylthio butanenitrile is contacted with ammonia or a solution of ammonium and water, to produce a mixture containing 2-amino-4-methylthio butanenitrile. The molar amount of ammonia relative to 2-hydroxy-4-methylthio butanenitrile is suitably from 3 to 10, preferably from 4 to 7. Where it is desired to use an aqueous solution of ammonia, the solution is suitably at a concentration greater that 25% by weight, preferably greater than 60% by weight. Preferably, the 2-hydroxy-4-methylthio butanenitrile is contacted with pure ammonia.

This first step of this process is suitably carried out at a temperature of from 40 to 80° C., preferably from 70 to 75° C. and under a pressure of from 10 to 30 bar, preferably from 15 to 25 bar. The reaction may be carried out in a stirred or tubular reactor with, in particular, a piston-type flow with a calorific exchange system or using a combination of the two reactors.

At the end of the reaction of the first step it is likely that there exists excess unreacted ammonia. The unreacted ammonia is preferably removed from the reactor. This may be implemented by flash depressurisation or by entrainment with an inert gas such as nitrogen. The temperature during this separation step is suitably below 60° C., preferably between 10 and 40° C. The pressure may be atmospheric pressure or sub atmospheric pressure or slightly above atmospheric pressure. Preferably a pressure of from 0.1 to 0.5×10$^5$ Pa is used. The ammonia recovered from the reaction may then be condensed or sent to a recovery section for further treatment.

The 2-amino-4-methylthio butanenitrile, produced in the first step of the process, is then hydrated in the presence of a ketone and an alkali metal hydroxide to produce methionine amide. The ketone is suitably present in a concentration of from 0.1 to 1, preferably 0.2 to 0.5 equivalent of ketone. The alkali metal hydroxide salt is suitably present in a concentration of from 0.05 to 0.5, preferably from 0.1 to 0.25 equivalent of alkali metal hydroxide. Preferably the ketone is acetone. Suitably the alkali metal hydroxide is potassium hydroxide or sodium hydroxide, especially sodium hydroxide.

The hydration step is suitably carried out at a temperature of from 10 to 40° C., preferably from 15 to 30° C. Suitably the reaction is carried out under atmospheric pressure. The reaction may be carried out in a stirred or in a tubular reactor or in a column packed with suitable packing material with a calorific exchange system.

By-products to this particular reaction include the alkali metal salt of methionine, residue 2-amino-4-methylthio butanenitrile, imidazolidinone (2,2'-dimethyl-5(methyl thio ethyl)-4-imidazolidinone), water, ammonia, unreacted ketone and the alkali metal hydroxide. The unreacted ketone, ammonia and at least part of the water in the product stream are then separated from the other components. To facilitate this separation step, the product stream may be distilled or stripped or by any other suitable separation technique. Where the product stream is distilled or stripped, the stripped comprising the separated ketone, water and ammonia stream may be partially condensed and the condensed phase returned to the aminoamide synthesis reactor. This separation step may be carried out under atmospheric or elevated pressure. The remaining uncondensed portion, also comprising unreacted ketone, water and ammonia may be sent to a recovery section for further treatment.

The methionine amide devoid of ketone, and ammonia, is then hydrolysed in the presence of the titanium-containing catalyst as hereinbefore described to produce the ammonium methioninate salt. The salt is then treated to remove ammonia as hereinbefore discussed, to obtain methionine.

The process of the present invention may comprise a recover section which is capable of receiving the unreacted and/or recovered ammonia, ketone and water from any stage of the process. Suitably, the three components are separated in the recovery section by absorption and distillation. The absorption step may be carried out using water or by an acid/base exchange reaction. The ammonia obtained after such treatment may then be recycled to the aminonitrile synthesis reactor whilst the ketone and water may be recycled to the aminoamide synthesis reactor As indicated above, the product stream obtained from the second step of the aforementioned industrially applicable process produces by-products including the alkali metal salt of methionine. Such by-products may be removed from the amide product stream by incorporating into the process, a further treatment step which comprises contacting the stream comprising such salts with a resin to facilitate an exchange process of the alkali metal ion with the resin. In a preferred embodiment of the present industrially applicable process, the second product stream resin, which is devoid of ketone, ammonia and, is contacted with the resin; namely after step (c) but before step (d) of the process.

Alternatively, the resin may be placed at the end of the overall process such that final product stream comprising methionine which is free of ammonia, is contacted with the resin.

Where the product stream is contacted with a resin, the alkali metal of the alkali metal methioninate salt is retained on the ion-exchange resin, thereby providing a solution containing methionine, free of alkali metal ions. Suitable resins are acidic resins, particularly sulphonic resins. Commercially available resins sold under the trade names Rohm & Haas IMAC C16P and Fluka Amberlist 15 may be used. Also suitable, are carboxylic acid resins wherein the $pK_a$ of the acid is less than 6.2, Suitable resins are resins such as those sold under the trade name Fluka Duolite C464 or Rohm & Haas IRC50, It is preferred to use a carboxylic acid resin.

Suitably, the stream comprising the alkali metal salt is passed continuously over the resin. When the resin is saturated with the alkali metal ion, the resin is suitably regenerated by displacing the metal ions. The metal ions may be displaced by treatment in acidic medium for example with a strong inorganic acid, such as sulphuric acid or hydrochloric acid. Molar amounts of inorganic acid corresponding to 2 to 14 mol, preferably 3 to 6 mol of acid per kg of resin may be used. The carboxylic acid resin may alternatively be regenerated by treating the resin with carbon dioxide in an aqueous medium under pressure of typically 10 to 25 bar. The regeneration is suitably carried out with a molar amount of acid corresponding to 2 to 14, preferably from 3 to 6 mol acid per kg of resin.

The final resulting product stream comprising free methionine in the liquid form may be used as is or optionally it may be further treated to recover solid methionine. This may be achieved by separating the methionine using any suitable separation method, for example by simple crystallisation after concentration or by atomisation after partial concentration, crystallisation and grinding, or by granulation after concentration.

The present invention will now be illustrated with the reference to the following examples:

EXAMPLE 1

Preparation of Titanium Catalyst

Ten titanium-containing catalysts, according to the present invention, and two catalysts not according to the present invention were prepared as follows:

(1) Catalyst 1: 55 g of powdered wet titanium oxide was placed in a Brabender™ mixer. A solution of nitric acid (6.26 g) and water (27.39 g) was slowly added to the powder and the resulting mixture stirred for 30 minutes at a speed of 50 turns per minute. The paste was then extruded at a speed of 4 cm per minute using an die having a diameter of 1.6 mm to provide a extrudate having a diameter of 1.6 mm.

The resulting extrudate was placed in an oven and the temperature increased from 120° C. to 480° C. at a rate of 3° C. per minute. The temperature was maintained at this level for four hours before reducing the temperature to ambient temperature at a rate of 5° C. per minute.

The weight loss of the paste was 38.5%.

(2) Catalyst 2: 59.2 g of powdered wet titanium oxide was placed in a Brabender™ mixer. A solution of nitric acid (5.65 g) and water (15.16 g) was slowly added to the powder and the resulting mixture stirred for 30 minutes at a speed of 50 turns per minute. The paste was then extruded at a speed of 4 cm per minute using an die having a diameter of 1.6 mm to provide a extrudate having a diameter of 1.6 mm.

The resulting extrudate was placed in an oven and the temperature increased from 120° C. to 480° C. at a rate of 3° C. per minute. The temperature was maintained at this level for four hours before being decreased to ambient temperature at a rate of 5° C. per minute.

The weight loss of the paste was 40%.

(3) Catalyst 3: This catalyst is a commercially available catalyst, obtained from Procatalyse, identified as CRS31.

(4) Catalyst 4: This catalyst is a commercially available catalyst, obtained from Degussa, identified as 7708.

(5) Catalyst 5: 228 g of powdered wet titanium oxide, 9.12 g of methyl cellulose and 4.56 g of polysaccharide were mixed in a Brabender™ mixer for 30 minutes. 119.39 g of water was then added to form a paste. The paste was kneaded for 120 minutes and then left for 1 hour. The paste was then extruded at a speed of 4 cm per minute to provide a extrudate having a diameter of 1.00 mm. The resulting extrudates were then placed in an oven and the temperature increased from 20° C. to 140° C. at a rate of 1° C. per minute over a two hours period. The temperature was then increased to 480° C. at a rate of 3° C. per minute over a period of 4 hours.

The weight loss of the paste was 45% and the percentage of methyl cellulose and polysaccharide in the paste was 2% in each case.

(6) Catalyst 6: The procedure used in the preparation of catalyst 5 was repeated except that the weight loss of the paste was 45% and the diameter of the extrudate was 1.6 mm.

(7) Catalyst 7: The procedure used in the preparation of catalyst 6 was repeated except that the weight loss of the paste was 45%, the percentage of methyl cellulose was 4% and the diameter of the extrudate was 1.6 mm.

(8) Catalyst 8: The procedure carried out for Catalyst 1 was repeated except that the weight loss of the paste was 40%.

Comparative Catalysts 1, not according to the present invention, is a commercially available catalyst obtained from Degussa, identified as 7709, Comparative Catalysts 2, not according to the present invention, is a commercially available catalyst obtained from Engelhard, identified as Ti-0720.

(9) Catalyst 9: 55 g of powdered titanium oxide was placed in a Brabender™ mixer. A solution of nitric acid (concentrated at 68%) (6.26 g) and water (20.57 g) was slowly added to the powder and the resulting mixture stirred for 30 minutes at a speed of 50 turns per minute. The paste was then extruded at a speed of 4 cm per minute using a three leaf clover die.

The resulting extrudate was placed in an oven and the temperature increased from 120° C. to 480° C. at a rate of 3° C. per minute. The temperature was maintained at this level for four hours before reducing the temperature to ambient temperature at a rate of 5° C. per minute. The calcinated extrudates had an external diameter of 0.8 mm. The weight loss of the paste was 35%.

(10) Catalyst 10: The procedure carried out for Catalyst 9 was repeated except that the external diameter of the calcinated extrudate was 1.6 mm.

Comparative Catalysts 1, not according to the present invention, is a commercially available catalyst obtained from Degussa, identified as 7709, Comparative Catalysts 2, not according to the present invention, is a commercially available catalyst obtained from Engelhard, identified as Ti-0720, A summary of the properties of the catalysts prepared as described above is given in Table 1

TABLE 1

CHARACTERISTICS OF THE CATALYST

| CATALYST | SHAPE | EXTERNAL DIAMETER (mm) | SURFACE AREA ($m^2/g$) | PORE VOLUME ($cm^3/g$) | MESOPORE POROSITY (nm) | MACROPORE POROSITY (nm) |
|---|---|---|---|---|---|---|
| 1 | extrudate | 1.6 | 63 | 0.38 | 17 | 200 |
| 2 | extrudate | 1.4 | 79 | 0.30 | 12 | 100 |
| 3 | extrudate | 4.0 | 115 | 0.29 | 10 | 100 |
| 4 | extrudate | 3.2 | 45 | 0.39 | 30 | — |
| 5 | extrudate | 0.8 | — | 0.44 | 9 | 150–160 |
| 6 | extrudate | 1.4 | — | 0.43 | 8 | 150–160 |
| 7 | extrudate | 1.3 | — | 0.44 | 9 | 150–160 |
| 8 | extrudate | 1.5 | 63 | 0.45 | 17 | 200 |
| 9 | three leaf clover | 0.8 | 100 | 0.36 | 14 | 50 |
| 10 | three leaf clover | 1.6 | 100 | 0.34 | 14 | 50 |
| Comparative catalyst 1 | extrudate | 3.2 | 12 | — | 35 | — |
| Comparative catalyst 2 | tablet | 3.3 | 177 | 0.36 | 6 to 20 | — |

EXAMPLE 2

Hydrolysis of Methionine Amide Using Powdered Catalyst

Catalysts 1, 2, 3, 4 9 prepared as detailed above and Comparative Catalysts 1 and 2 were ground to a powdered form and used to hydrolyse methionine amide. An aqueous solution of the methionine amide was placed in a batch reactor with 10 g of the powdered catalyst suspended in water to give an initial ratio of catalyst to amide of 1 g of catalyst per gram of methionine amide. The initial concentration of amide in the reactor was 0.5 mole/kg.

The reaction was carried out at a temperature of between 95 and 100° C. and under atmospheric pressure.

The product obtained (i.e., ammonium methioninate or "MTN") was analysed using HPLC and the yield and conversion determined.

The results are given in FIG. 1 where "TT AMTBM" stands for total conversion of AMTBM and "RR MTN" stands for total yield of MTN.

EXAMPLE 3

Hydrolysis of Methionine Amide Using Catalyst in a Fixed Bed Reactor with Recirculation Catalysts 3, 5, 6 and 7 were used in the extrudate form to hydrolyse methionine amide in the amounts as given in Table 2, The catalyst was placed in a fixed bed reactor. 216 g of water was added to the reactor. The temperature was increased to 95° C. 122.9 g (21.7% p/p) of methionine amide was then added to provide an initial concentration of amide of 0.5 mol/kg The product obtained was analysed using HPLC and the yield and conversion determined.

Figure 2:
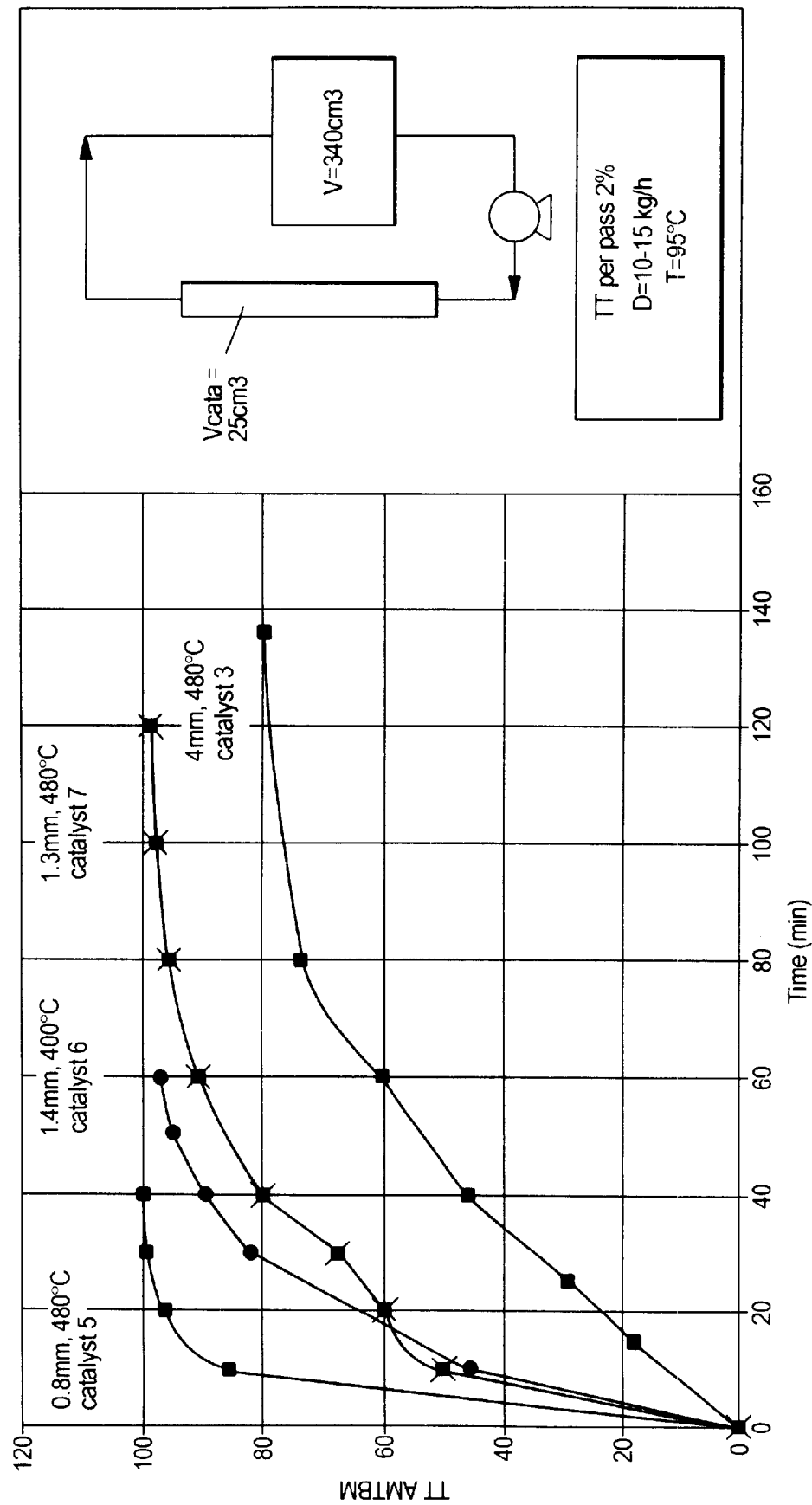
FIG. 2 is a graph of TT AMTBM versus time for the catalysts of Example 3.

The results are given in FIG. 2

TABLE 2

| CATALYST | WEIGHT OF CATALYST (g) | FEED FLOW RATE (kg/hour) | DIAMETER (mm) | CALCINATION TEMPERATURE (° C.) |
|---|---|---|---|---|
| 3 | 40 | 10–15 | 4 | 480 |
| 5 | 20 | 5 | 0.8 | 480 |
| 6 | 20 | 10–15 | 1.4 | 400 |
| 7 | 22 | 10–15 | 1.3 | 480 |

EXAMPLE 4

Hydrolysis of Methionine Amide Using Catalyst in a Fixed Bed Reactor with Plug Flow (a) under atmospheric pressure Catalysts 4, 6 and 8 were used in the extrudate form to hydrolyse methionine amide. A solution of methionine amide having an initial concentration of between 0.37 and 0.85 mol/kg was placed in the reactor. The reactor temperature was set at 95° C. A weight of catalyst, as given in Table 3, was placed in the reactor and the process operated under the conditions given in Table 3.

TABLE 3

| CATALYST | WEIGHT OF CATALYST (g) | CONC. OF AMIDE (moles) | FEED FLOW RATE (g/hour) | TIME ON STREAM* (minutes) |
|---|---|---|---|---|
| 4 | 30 | 0.37 | 168.8, 153.8 | 4.8, 5.3 |
| 4 | 30 | 0.37 | 210.8 | 3.8 |
| 6 | 5 | 0.37 | 223 | 0.6 |
| 6 | 5 | 0.37 | 162 | 0.8 |
| 6 | 30 | 0.37 | 145, 188.9, 212.8 | 5.5, 4.2, 3.7 |
| 6 | 30 | 0.83 | 178, 218, 250 | 3.2, 3.7, 4.5 |
| 8 | 40 | 0.84 | 120, 160, 220 | 4.8, 6.7, 8.9 |

Figure 3:
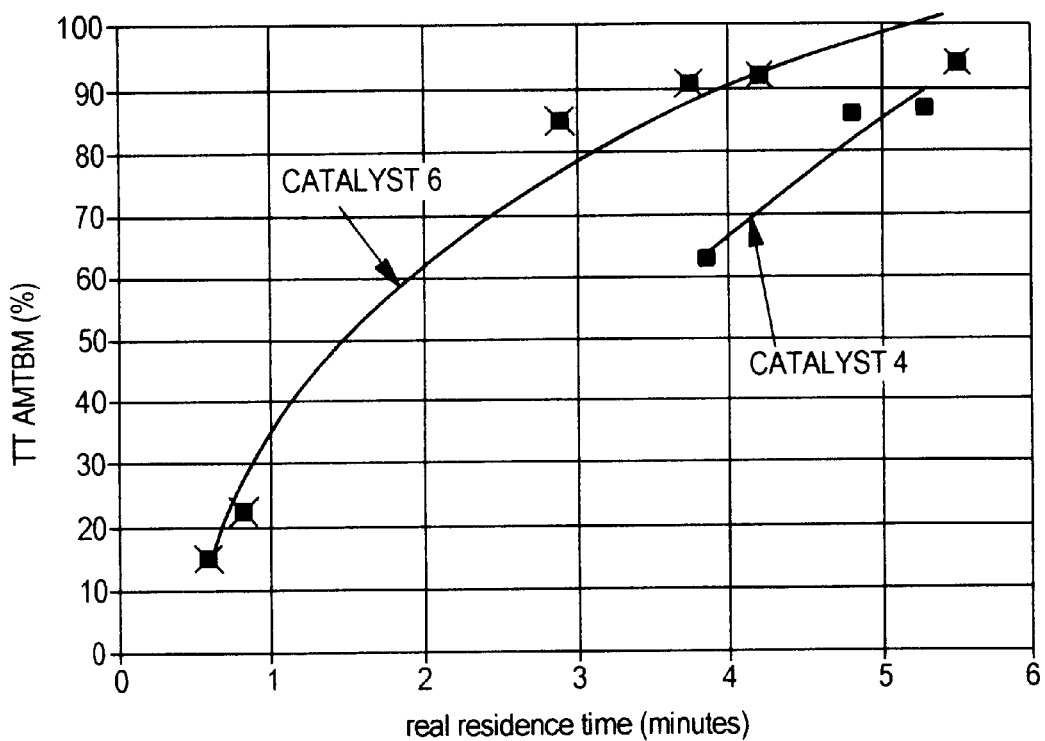
FIG. 3 is a graph of TT AMTBM versus time for catalysts 4 and 6 of Example 4.
Figure 4:
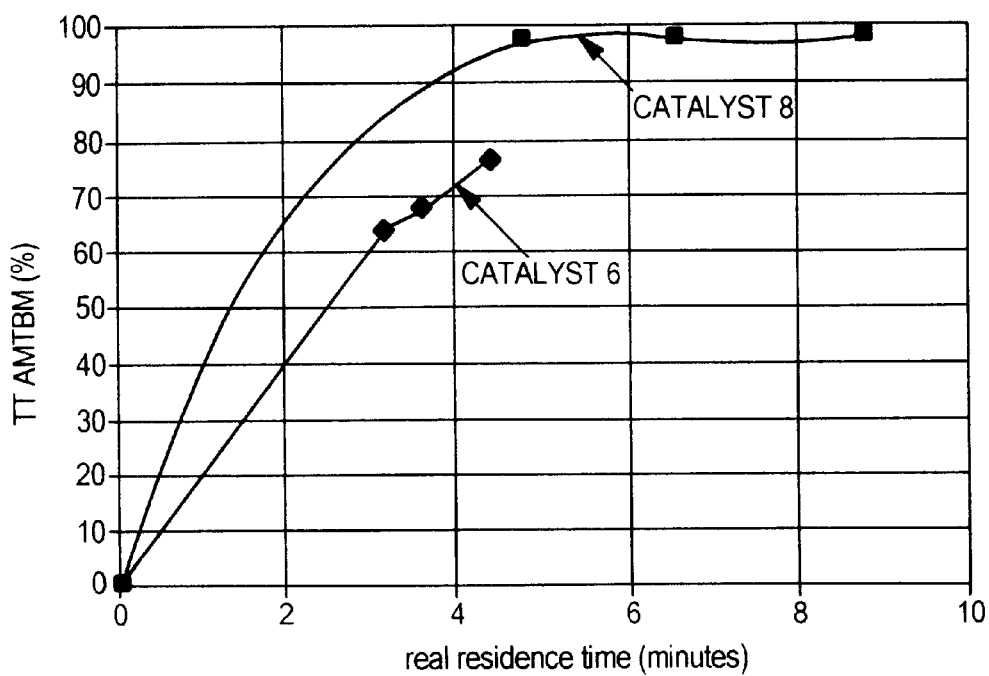
FIG. 4 is a graph of TT AMTBM versus time for catalysts 6 and 8 of Example 4.

*Time on stream (ts) is calculated as follows:
ts = (60 × Em × Wgt of catalyst (g))/flow rate (g/h) where
Em = (weight of liquid)/weight of dry catalyst + weight of liquid)
Em = 0.45 for the catalysts of the present invention The results are given in FIG. 3
(b) under Elevated Pressure The above procedure was repeated in a fixed bed using catalysts of different diameter and amounts. The conversion of amide is reported in Table 4 below.

TABLE 4

| CATALYST | TEMP. (° C.) | WEIGHT OF CATALYST (g) | FEED FLOW RATE (g/h) | CONVERSION (%) |
|---|---|---|---|---|
| 8 | 100 | 40 | 120 | 97.5 |
| 8 | 100 | 40 | 300 | 87 |
| 8 | 100 | 40 | 300 | 95.5 |
| 9 | 100 | 20 | 120 | 97.5 |
| 9 | 100 | 20 | 300 | 93.3 |
| 9 | 120 | 20 | 300 | 95.8 |
| 10 | 100 | 20 | 120 | 95.6 |
| 10 | 100 | 20 | 300 | 82.6 |
| 10 | 120 | 20 | 300 | 90.5 |
| 10 | 100 | 40 | 120 | 98.2 |
| 10 | 100 | 40 | 300 | 97 |
| 10 | 120 | 40 | 300 | 98 |

The time on stream was calculated as in the previous example.

EXAMPLE 5

Industrial Process for the Preparation of Methionine

Figure 5:
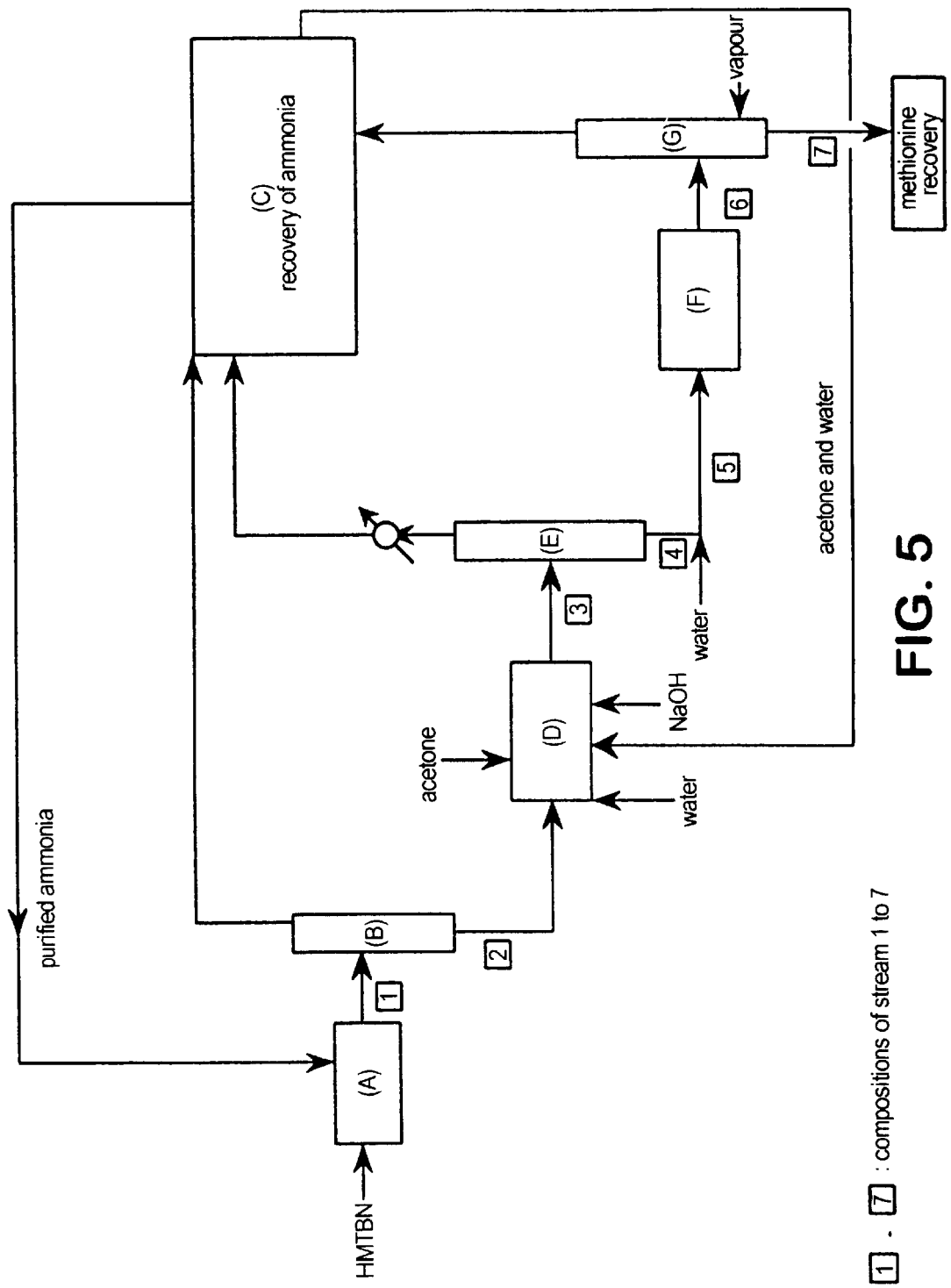
FIG. 5 is a reaction scheme to obtain methionine which does not use a resin (embodiment 1 of the invention).
Figure 6:
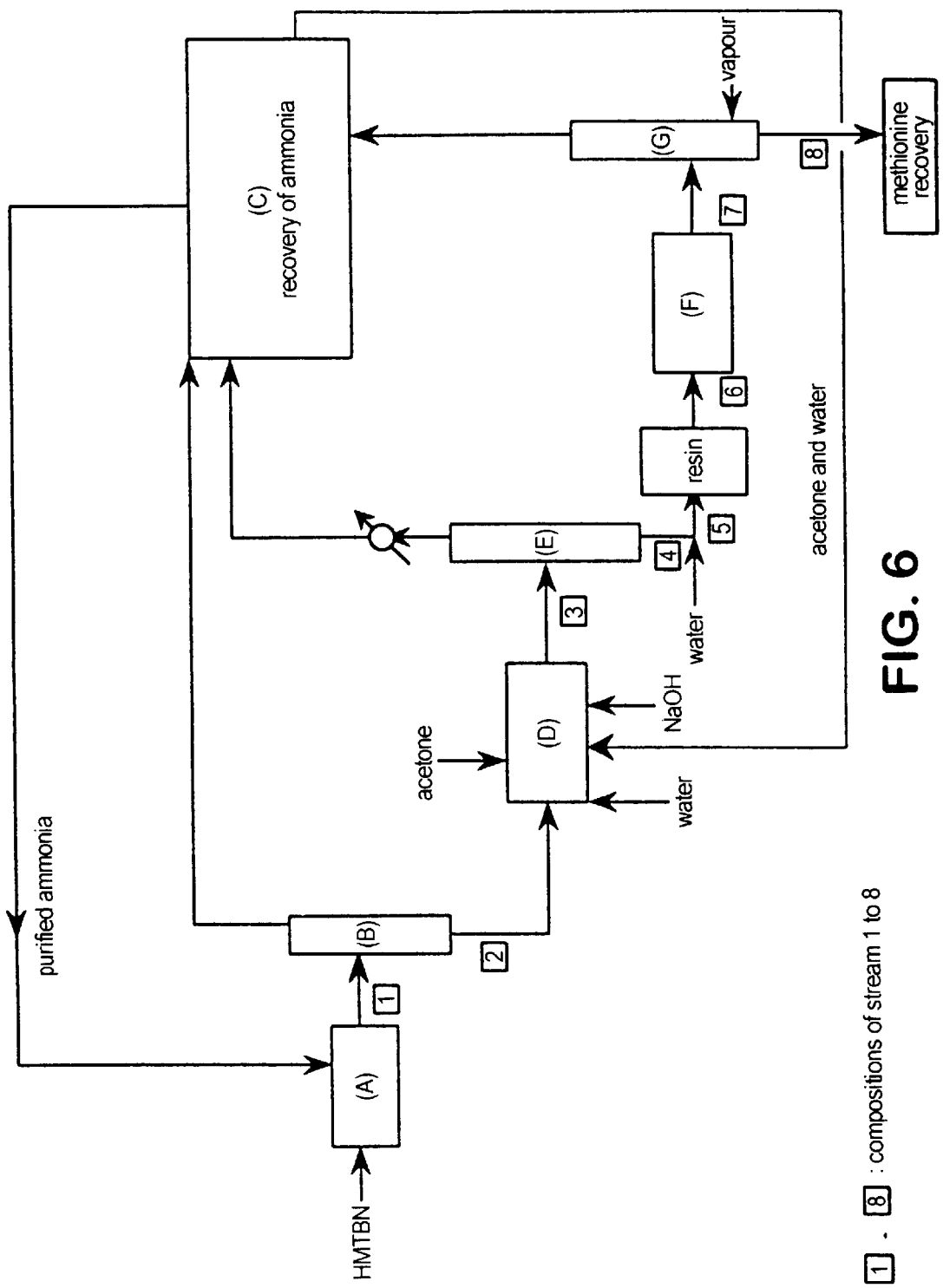
FIG. 6 is a reaction scheme to obtain methionine free from alkali metal salt using a resin prior to hydrolysis (embodiment 2 of the invention).
Figure 7:
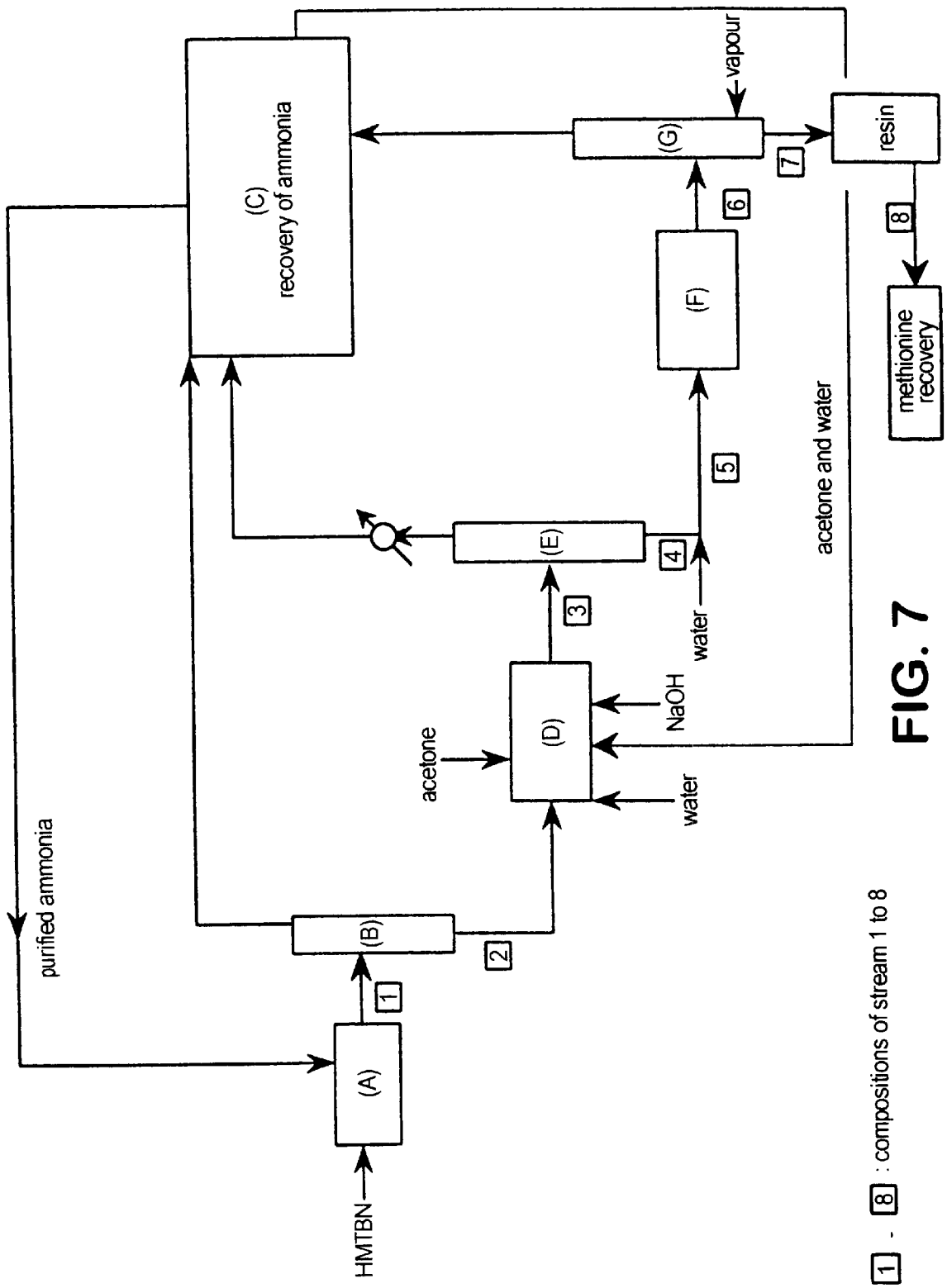
FIG. 7 is a reaction scheme to obtain methionine free from alkali metal salt using a resin after hydrolysis (embodiment 3 of the invention).

Catalyst Number 9, prepared according to Example 1, was used in the industrial process. The overall reaction scheme is represented by FIG. 5. In order to obtain methionine, free from alkali metal salt, a resin was used in the process. The resin was placed in two positions hereinafter referred to as embodiment 2 and embodiment 3 as shown in FIGS. 6 and 7 respectively. The composition of the streams at each stage of the three processes is given in Tables 5, 6 and 7 respectively.

Embodiment (1)—Synthesis of Methionine: The 2-hydroxy-4-methylthio butane nitrile is reacted with ammonia in reactor (A) to provide a mixture comprising 2-amino-4-methylthio butanenitrile (composition 1). The unreacted ammonia is separated from the product stream in Vessel (B) and passed to recovery section (C). The treated stream (composition 2) is passed to reactor (D). Acetone, water and sodium hydroxide are fed into the reactor (D). The resulting product stream comprising methionine amide (composition 3) is treated by withdrawing the unreacted acetone, ammonia and at least part of the water in column (E). The stripped gases are partially condensed and sent to recovery section (C). Water is added to the resulting amide solution (composition 4) and the solution (composition 5) is contacted with the titanium catalyst in reactor (F). The product stream comprising ammonium methioninate (composition 6) is treated to liberate ammonia and form the free methionine by stripping in an ammonia stripper (G). The liberated ammonia is condensed and sent to the recovery section (C). The liquid free methionine (composition 7) can then be acidified and treated further to obtain solid methionine.

The recovery section (C) comprises a first absorber, a heating column, a second absorber and a distillation column (not shown). The stripped gases from column (E) and the stripped gases from the ammonium stripper (G) are passed to the first absorber which is fed with a solution of monoammonium phosphate (5.5 w/w % ammonia, 24.5 w/w % $H_3PO_4$ and 70 w/w % water). The gas stream entering the column has a composition of (40.6 w/w % ammonia, 8 w/w % acetone and 51.4 w/w % water). The absorber is fitted with a heat exchanger to withdraw the dissolution heat of ammonia. Liquid exiting the bottom of the absorber column at 111.8° C. comprises 7.8 w/w % ammonia, 23.9 w/w % $H_3PO_4$ and 68.3 w/w % water and traces of acetone. The gas exiting the top of the absorber column at 111.9° C. comprises 13.1% acetone, 0.9 w/w % ammonia and 86 w/w % water. This gaseous mixture is condensed and recycled to the aminoamide synthesis reactor. The liquid mixture obtained from the bottom of the absorber column is fed to a heating column to liberate ammonia. The mixture is heated and stripped by water vapour at 130° C. to recover the ammonia. A gas mixture obtained from the top of the heating column comprises 18 w/w % ammonia and 82 w/w % water. This gas is condensed and mixed with the unreacted ammonia stripped from Vessel (B) in a water absorber (the second absorber) to give an aqueous solution comprising 25 w/w % ammonia, 74.9 w/w % water and 0.1% acetone. This mixture is distilled to recover pure ammonia which is then recycled back to the aminonitrile synthesis reactor. The liquid mixture exiting the bottom of the heating column is recycled back to the absorbing column after withdrawal of heat.

Embodiment (2)—Synthesis of Methionine Using a Resin Prior to Hydrolysis: The 2-hydroxy-4-methylthio butanenitrile is reacted with ammonia in reactor (A) to provide a mixture comprising 2-amino-4-methylthio butanenitrile (composition 1). The unreacted ammonia is separated from the product stream in Vessel (B) and passed to recovery section (C). The treated stream (composition 2) is passed to reactor (D). Acetone, water and sodium hydroxide are fed into the reactor (D). The resulting product stream comprising methionine amide (composition 3) is treated by withdrawing the unreacted acetone, ammonia and at least part of the water in column (E). The stripped gases are partially condensed and sent to recovery section (C). Water is added to the resulting amide solution (composition 4) and the solution (composition 5) is then continuously contacted with the resin. The resulting stream (composition 6), which does not contain sodium salts, is contacted with the titanium catalyst in reactor (F). The product stream comprising ammonium methioninate (composition 7) is treated to liberate ammonia and isolate the free methionine by stripping in an ammonium stripper (G). The liquid free methionine (composition 8) may be treated further to obtain solid methionine. The recovery section is as detailed in embodiment 1, Embodiment (3)—Synthesis of Methionine Using a Resin After Hydrolysis: The 2-hydroxy4-methylthio butanenitrile is reacted with ammonia in reactor (A) to provide a mixture comprising 2-amino-4-methylthiobutanenitrile (composition 1). The unreacted ammonia is separated from the product stream in Vessel (B) and passed to recovery section (C). The treated stream (composition 2) is passed to reactor (D). Acetone, water and sodium hydroxide are fed into the reactor (D). The resulting product stream comprising methionine amide (composition 3) is treated by withdrawing the unreacted acetone, ammonia and at least part of the water in column (E). The stripped gases are partially condensed and sent to recovery section (C). Water is added to the resulting amide solution (composition 4) and the resulting stream (composition 5) is then contacted with the titanium catalyst in reactor (F). The product stream comprising ammonium methioninate and sodium methioninate (composition 6) is treated to liberate ammonia and to obtain the free methionine by stripping in an ammonium stripper (G). The resulting stream (composition 7) is then continuously contacted with the resin. The resulting stream (composition 8) which does not contain sodium salts may be treated further to obtain solid methionine. The recovery section is as detailed in embodiment 1.

TABLE 5

|  | N° 1 Aminonitrile solution before ammonia separation | N° 2 Aminonitrile solution after ammonia separation | N° 3 Amide solution before removing acetone and NH3 and water dilution | N° 4 Amide solution after removing acetone and NH3 | N° 5 Amide solution after water dilution | N° 6 Resulting solution after contacting with TiO2 | N° 7 Resulting solution after separating ammonia |
|---|---|---|---|---|---|---|---|
| % w/w |  |  |  |  |  |  |  |
| Hydoxy nitrile | 0 | 0 | 0 | 0 | 0 | 0 | 0 |
| Amino nitrile | 50.70 | 67.10 | 0 | 0 | 0 | 0 | 0 |
| Amide | 0 | 0 | 26.10 | 30.90 | 10.20 | 0.03 | 0.03 |
| MTN Na | 0 | 0 | 5.97 | 7.36 | 2.43 | 2.43 | 2.43 |
| MTN-NH4 | 0 | 0 | 0 | 0 | 0 | 11.41 | 0 |
| free MTN | 0 | 0 | 0 | 0 | 0 | 0 | 10.25 |
| NH3 | 27.70 | 7.15 | 7.20 | 0.15 | 0.05 | 0.05 | 0 |
| Acetone | 0 | 0 | 4.00 | 0.01 | 0.00 | 0.03 | 0 |
| IDZ | 0 | 0 | 1.20 | 1.30 | 0.43 | 0.33 | 0.27 |
| water | 21.60 | 25.75 | 55.53 | 60.28 | 86.89 | 85.72 | 87.02 |
| T ° C. | 70 | 20 | 35 | 102 | 57 | 100 | 100 |
| pressure (bars) | 20 | 1 | 1 | 1 | 1 | 3 | 1 |

TABLE 6

|  | N° 1 Aminonitrile solution before ammonia separation | N° 2 Aminonitrile solution after ammonia separation | N° 3 Amide solution before removing acetone and NH3 and water dilution | Amide solution after removing acetone and NH3 | N° 5 Amide solution after water dilution | N° 6 Amide solution after contacting with resin | N° 7 Resulting solution after contacting with TiO2 | N° 8 Resulting solution after separating ammonia |
|---|---|---|---|---|---|---|---|---|
| % w/w |  |  |  |  |  |  |  |  |
| Hydoxy nitrile | 0 | 0 | 0 | 0 | 0 | 0 | 0 | 0 |
| Amino nitrile | 50.70 | 67.10 | 0 | 0 | 0 | 0 | 0 | 0 |
| Amide | 0 | 0 | 26.10 | 30.90 | 9.90 | 9.90 | 0.04 | 0.04 |
| MTN Na | 0 | 0 | 5.97 | 7.36 | 2.36 | 0 | 0 | 0 |
| MTN-NH4 | 0 | 0 | 0 | 0 | 0 | 0 | 11.15 | 0 |
| free MTN | 0 | 0 | 0 | 0 | 0 | 2.06 | 2.06 | 12.07 |
| NH3 | 27.70 | 7.10 | 7.20 | 0.15 | 0.05 | 0 | 0 | 0 |
| acetone | 0 | 0 | 4.00 | 0.01 | 0.00 | 0 | 0.03 | 0 |
| IDZ | 0 | 0 | 1.20 | 1.30 | 0.42 | 0.42 | 0.32 | 0.26 |
| water | 21.60 | 25.80 | 55.53 | 60.28 | 87.27 | 87.62 | 86.40 | 87.63 |
| T ° C. | 70 | 20 | 30 | 100 | 50 | 50 | 100 | 100 |
| pressure (bars) | 20 | 1 | 1 | 1 | 1 | 1 | 3 | 1 |

TABLE 7

|  | N° 1 Aminonitrile solution before ammonia separation | N° 2 Aminonitrile solution after ammonia separation | N° 3 Amide solution before removing acetone and NH3 and water dilution | N° 4 Amide solution after removing acetone and NH3 | N° 5 Amide solution after water dilution | N° 6 Resulting solution after contacting with TiO2 | N° 7 Resulting solution after separating ammonia | N° 8 Resulting solution after contacting with resin |
|---|---|---|---|---|---|---|---|---|
| % w/w |  |  |  |  |  |  |  |  |
| Hydoxy nitrile | 0 | 0 | 0 | 0 | 0 | 0 | 0 | 0 |
| Amino nitrile | 50.70 | 67.10 | 0 | 0 | 0 | 0 | 0 | 0 |
| Amide | 0 | 0 | 26.10 | 30.90 | 9.90 | 0.05 | 0.05 | 0.05 |
| MTN Na | 0 | 0 | 5.97 | 7.36 | 2.36 | 2.36 | 2.36 | 0 |
| MTN-NH4 | 0 | 0 | 0 | 0 | 0 | 11.14 | 0 | 0 |

TABLE 7-continued

|  | N° 1 Aminonitrile solution before ammonia separation | N° 2 Aminonitrile solution after ammonia separation | N° 3 Amide solution before removing acetone and NH3 and water dilution | N° 4 Amide solution after removing acetone and NH3 | N° 5 Amide solution after water dilution | N° 6 Resulting solution after contacting with TiO2 | N° 7 Resulting solution after separating ammonia | N° 8 Resulting solution after contacting with resin |
|---|---|---|---|---|---|---|---|---|
| free MTN | 0 | 0 | 0 | 0 | 0 | 0 | 10.05 | 12.11 |
| NH3 | 27.70 | 7.10 | 7.20 | 0.15 | 0.05 | 0.05 | 0 | 0 |
| acetone | 0 | 0 | 4.00 | 0.01 | 0.00 | 0.03 | 0 | 0 |
| IDZ | 0 | 0 | 1.20 | 1.30 | 0.42 | 0.32 | 0.26 | 0.26 |
| water | 21.60 | 25.80 | 55.53 | 60.28 | 87.27 | 86.05 | 87.28 | 87.58 |
| T ° C. | 70 | 20 | 30 | 100 | 50 | 100 | 100 | 100 |
| pressure (bars) | 20 | 1 | 1 | 1 | 1 | 3 | 1 | 1 |

What is claimed is:

1. A process for the production of methionine, said process capable of industrial application, which comprises:
    (a) contacting 2-hydroxy-4-methylthio butanenitrile with ammonia or a solution containing ammonia to produce a first product comprising 2-amino-4-methylthio butanenitrile,
    (b) reacting the 2-amino-4-methylthio butanenitrile with a ketone and an alkali metal hydroxide in a reactor to produce a second product comprising methionine amide,
    (c) removing any unreacted ketone and ammonia from the second product stream,
    (d) hydrolysing the methionine amide in the presence of a catalyst comprising titanium to produce a third product stream comprising ammonium methioninate, said catalyst having a porosity of from 5 to 1000 nm, a total pore volume of from 0.2 to 0.55 cm$^3$/g and a surface area of from 30 to 150 m$^2$/g, and
    (e) liberating methionine from the ammonium methioninate,
wherein the methionine amide is contacted with an acidic resin prior to the hydrolysis.

2. A process as claimed in claim 1 wherein water is also removed from the second product stream in step (c) and the unreacted and/or recovered ammonia, ketone and water are sent to a recovery section and the ammonia is separated from the ketone and water.

3. A process as claimed in claim 2 wherein the separation is carried out by absorption and distillation.

4. A process as claimed in claim 2 wherein the separated ammonia is recycled to become at least part of the ammonia used in step (a).

5. A process as claimed in claim 2 wherein the separated ketone and water are recycled to the reactor in step (b).

6. A process as claimed in claim 1, in which the catalyst has a macroporous distribution of from 5 to 100 nm and from 20 to 1000 nm.

7. A process as claimed in claim 1, in which the total pore volume of said catalyst is from 0.25 to 0.45 cm$^3$/g.

8. A process as claimed in claim 1, wherein the surface area of said catalyst is from 40 to 120 m$^2$/g.

9. A process as claimed in claim 1, in which the catalyst is in particulate form and the diameter of the catalyst particles is from 0.05 to 2 mm.

10. A process as claimed in claim 1, in which the catalyst comprises TiO$_2$, Ti—W, TiMo, Ti—Si—W, Ti—Nb—Mo, Ti—Zr, Ti—Al, Ti—Cr, Ti—Zn, Ti—V or a mixture thereof.

11. A process as claimed in claim 1, in which the catalyst comprises TiO$_2$.

12. A process as claimed in claim 1, in which the catalyst is present in an amount of from 0.1 to 2 g of catalyst per gram of amide.

13. A process as claimed in claim 1, wherein the hydrolysis is carried out at a temperature of from 50 to 150° C.

14. A process as claimed in claim 1, wherein the hydrolysis is carried out under a pressure of from 1 to 10 bar.

* * * * *